US009309180B2

(12) United States Patent
Kuppinger et al.

(10) Patent No.: US 9,309,180 B2
(45) Date of Patent: Apr. 12, 2016

(54) METHOD FOR PRODUCING ACRYLIC ACID

(71) Applicant: Evonik Degussa GmbH, Essen (DE)

(72) Inventors: Franz-Felix Kuppinger, Marl (DE); Florian Klasovsky, Haltern am See (DE); Alexander May, Seeheim-Jugenheim (DE); Min-Zae Oh, Cologne (DE)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 14/650,089

(22) PCT Filed: Jan. 14, 2014

(86) PCT No.: PCT/EP2014/050550
§ 371 (c)(1),
(2) Date: Jun. 5, 2015

(87) PCT Pub. No.: WO2014/111363
PCT Pub. Date: Jul. 24, 2014

(65) Prior Publication Data
US 2015/0315115 A1 Nov. 5, 2015

(30) Foreign Application Priority Data

Jan. 16, 2013 (DE) .......................... 10 2013 000 602

(51) Int. Cl.
*C07C 51/377* (2006.01)
*C08F 20/06* (2006.01)

(52) U.S. Cl.
CPC .............. *C07C 51/377* (2013.01); *C08F 20/06* (2013.01)

(58) Field of Classification Search
CPC ................................ C07C 51/377; C08F 20/06
USPC .............................................. 562/599; 526/75
See application file for complete search history.

(56) References Cited

U.S. PATENT DOCUMENTS

| 2,303,842 | A | 12/1942 | Kirk et al. |
| 7,332,624 | B2 * | 2/2008 | Nishimura ............ C07C 51/252 562/532 |
| 7,939,597 | B2 | 5/2011 | Bub et al. |
| 7,999,130 | B2 | 8/2011 | Ackermann et al. |
| 8,198,481 | B2 | 6/2012 | Kuppinger et al. |
| 8,207,371 | B2 | 6/2012 | Vogel et al. |
| 8,258,249 | B2 | 9/2012 | Bub et al. |
| 8,293,941 | B2 | 10/2012 | Kuppinger et al. |
| 8,362,299 | B2 | 1/2013 | Hengstermann et al. |
| 8,481,784 | B2 | 7/2013 | Kuppinger et al. |
| 8,524,945 | B2 | 9/2013 | Stochniol et al. |
| 8,569,539 | B2 | 10/2013 | May et al. |
| 8,703,450 | B2 | 4/2014 | Bub et al. |
| 8,841,481 | B2 | 9/2014 | Zanthoff et al. |
| 8,889,899 | B2 | 11/2014 | Ackermann et al. |
| 8,895,683 | B2 | 11/2014 | Kuppinger et al. |
| 2005/0221457 | A1 | 10/2005 | Tsobanakis et al. |
| 2009/0134357 | A1 | 5/2009 | Bub et al. |
| 2009/0209781 | A1 | 8/2009 | Ackermann et al. |
| 2009/0298144 | A1 * | 12/2009 | Tsobanakis ........... C07C 51/377 435/135 |
| 2010/0021977 | A1 | 1/2010 | May et al. |
| 2010/0068773 | A1 | 3/2010 | Marx et al. |
| 2010/0291644 | A1 | 11/2010 | Marx et al. |
| 2014/0135521 | A1 | 5/2014 | Koestner et al. |
| 2014/0180234 | A1 | 6/2014 | Bub et al. |

FOREIGN PATENT DOCUMENTS

| DE | 1 768 253 A1 | 10/1971 |
| WO | WO 03/082795 A2 | 10/2003 |
| WO | WO 2008/061819 A1 | 5/2008 |
| WO | WO 2008/145737 A1 | 12/2008 |
| WO | WO 2013/155245 A2 | 10/2013 |

OTHER PUBLICATIONS

German Search Report dated Aug. 7, 2013 for DE 10 2013 000 602.3, 5 pages.
International Search Report and Written Opinion (in German) mailed Apr. 4, 2014 for PCT/EP2014/050550, 8 pages.

* cited by examiner

*Primary Examiner* — Sikarl Witherspoon
(74) *Attorney, Agent, or Firm* — Philip P. McCann; John P. Zimmer; Smith Moore Leatherwood LLP

(57) ABSTRACT

Method for producing acrylic acid by dehydration of a $C_3$ hydroxycarboxylic acid, characterized in that dehydration is achieved by contacting, at a temperature of more than 150° C., the hydroxycarboxylic acid with a mixture which is liquid at this temperature and comprises at least one metal salt of a $C_3$ hydroxycarboxylic acid, and water.

15 Claims, 2 Drawing Sheets

METHOD FOR PRODUCING ACRYLIC ACID

This application is a national stage application under 35 U.S.C. §371 of International Application No. PCT/EP2014/050550 filed 14 Jan. 2014, which claims priority to German Application No. DE 10 2013 000 602.3 filed 16 Jan. 2013, the disclosures of which are expressly incorporated herein by reference.

FIELD

The present invention relates to a method for producing acrylic acid by dehydration of a $C_3$ hydroxycarboxylic acid by contacting, at a temperature of more than 150° C., the hydroxycarboxylic acid with a mixture which is liquid at this temperature and comprises at least one metal salt of a $C_3$ hydroxycarboxylic acid, and water.

BACKGROUND

Acrylic acid is an important intermediate used in particular in the form of its polymers. The best-known use of acrylic acid is the production of superabsorbent polymers based on polyacrylic acid.

Acrylic acid is conventionally chemically produced by oxidation of propene to give acrolein and subsequent further oxidation to afford acrylic acid.

Newer methods seek to produce acrylic acid using other feedstocks. For instance, WO 2008/061819 describes a method for producing (meth)acrylic acid (the term (meth) acrylic acid is intended to encompass both methacrylic acid and acrylic acid) where cyclic esters are converted into (meth) acrylic acid in the presence of a catalyst.

In recent years, economic and ecological considerations have spurred numerous attempts to use other feedstocks to produce acrylic acid or methacrylic acid, in particular renewable feedstocks.

For instance, WO 2008/145737 describes the production of methacrylic acid by dehydration of 3-hydroxyisobutyric acid which was produced in biotechnological fashion from renewable feedstocks, in particular from carbohydrates and/or glycerol. The dehydration is performed in the liquid phase at a pressure in the range of from 200 to 500 mbar and a temperature in the range of from 200° C. to 230° C. in the presence of alkali metal ions as catalyst.

DE-A 1 768 253 likewise describes such a method for producing methacrylic acid by dehydration of α-hydroxyisobutyric acid (HIBA) wherein said method is characterized in that HIBA is reacted in the liquid phase at a temperature of at least 160° C. in the presence of a dehydration catalyst consisting of a metal salt of alpha-hydroxyisobutyric acid. Particularly suitable here are the alkali metal and alkaline earth metal salts of HIBA which are produced in situ in an HIBA melt by reaction of suitable metal salts. This patent describes methacrylic acid yields of up to 95% based on HIBA and the feed for the continuous procedure consists of HIBA and about 1.5 wt % of HIBA alkali metal salt.

Neither of the aforementioned documents describe a method for producing acrylic acid.

WO 2013/155245 filed by Procter & Gamble describes the use of mixtures of phosphates as catalysts in the gas-phase dehydration of lactic acid to afford acrylic acid.

Gas-phase dehydrations require that the reactants are initially converted into the gas phase which often results, for example under the influence of thermal energy on the reactants, in decomposition of the reactants which manifests itself as coking for example.

It is therefore an object of the present invention to provide a method for producing acrylic acid from hydroxycarboxylic acids, which avoids the disadvantages of prior art methods.

SUMMARY

It has been found that, surprisingly, acrylic acid may be produced from hydroxycarboxylic acid by a method as described in the claims.

The present invention thus provides a method for producing carboxylic acids which is claimed in the claims and further described in the description which follows.

The method according to the invention has the advantage that acrylic acid may be prepared using lactic acid which may be obtained from renewable feedstocks.

The method according to the invention has the further advantage that it can switch between the feedstocks 3-hydroxypropionic acid and lactic acid depending on the available feedstock source.

A further advantage over a heterogeneous gas-phase dehydration in or at the phase boundary of the liquid phase is that prior complete evaporation of the organic acids may be eschewed. These evaporations suffer from severe coking since the evaporation temperature and decomposition temperature are close together. This can be minimized only by supplying a great deal of additional water which evaporates and also needs to be removed again in subsequent steps which is costly and inconvenient. Direct conversion at the salt melt makes it possible to eschew this severe dilution and to use concentrated solutions.

BRIEF DESCRIPTION OF THE DRAWINGS

The foregoing and other objects, features, and advantages of the product transport container will be apparent from the following more particular description of perferred embodiments as illustrated in the accompanying drawings in which reference characters refer to the same parts throughout the various views. The drawings are not necessarily to scale, emphasis instead being placed upon illustrating the principles of the invention.

DETAILED DESCRIPTION

Figure 1:
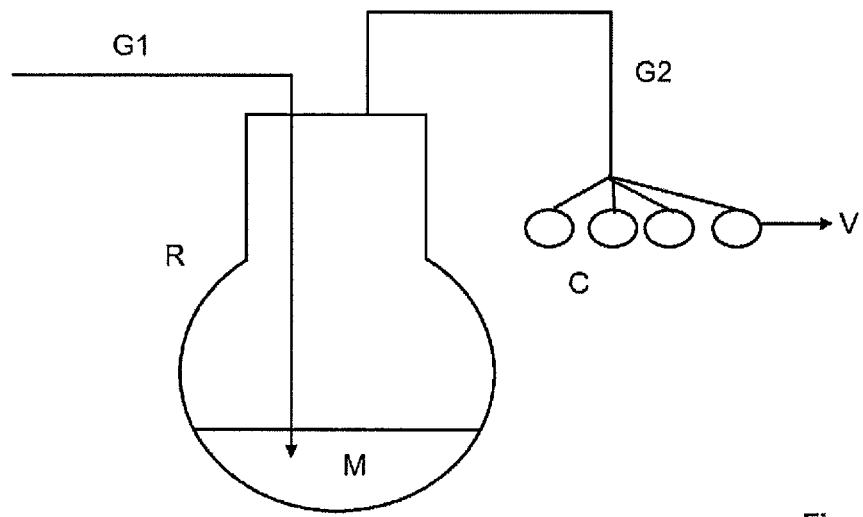
FIG. 1 is a schematic diagram of the experimental set-up of the present invention.

The subject matter provided by the invention is illustratively described hereinbelow without any intention to limit the invention to these illustrative embodiments. Where reference is made in what follows to ranges, general formulae or classes of compounds, these shall encompass not just the corresponding ranges or groups of compounds explicitly mentioned, but also all sub-ranges and sub-groups of compounds which are obtainable by extraction of individual values (ranges) or compounds. When documents are cited in the context of the present description, the contents thereof, particularly with regard to the subject matter that forms the context in which the document has been cited, are considered in their entirety to form part of the disclosure content of the present invention. Unless stated otherwise, percentages are figures in percent by weight. When average values are reported hereinbelow, the values in question are weight averages, unless stated otherwise. When parameters which have been determined by measurement are reported hereinafter, they have been determined at a temperature of 25° C. and a pressure of 101 325 Pa, unless stated otherwise.

The method according to the invention for producing acrylic acid by dehydration of a $C_3$ hydroxycarboxylic acid is characterized in that dehydration is achieved by contacting, at a temperature of more than 150° C., the hydroxycarboxylic acid with a mixture which is liquid at this temperature and comprises at least one metal salt of a $C_3$ hydroxycarboxylic acid, and water. It is preferable when the fraction of water based on the sum total of water and hydroxycarboxylic acid metal salt is from 0.5 to 95 wt %, preferably from 1 to 80 wt % and more preferably from 2 to 25 wt %.

The mixture may be prepared by admixing a solution of $C_3$ hydroxycarboxylic acid and water with a suitable metal salt, preferably a metal carbonate or one or more metal salts of formula (I)

$$M^{z+}{}_xH_{3-x*z}PO_4{}^{z*x-} \qquad (I)$$

where x=1 or 2, z=1 or 2 and M=metal, preferably alkali metal or alkaline earth metal, preferably Na, Ba or K, with the proviso that when z=2, x=1. The amount of metal salt added may be used to control whether any free acid remains in the mixture or not. It is preferable to add an amount of metal salt to the mixture such that the molar ratio of hydroxycarboxylic acid metal salt to free hydroxycarboxylic acid is from 100:1 to 1:100. When the metal salt employed is a metal carbonate, the molar ratio of hydroxycarboxylic acid metal salt to free hydroxycarboxylic acid is preferably from 10:1 to 2:1 and more preferably from 5:1 to 3:1. When the metal salt employed is a metal salt of formula (I), the molar ratio of hydroxycarboxylic acid metal salt to free hydroxycarboxylic acid is preferably from 1:50 to 1:10 and more preferably from 1:40 to 1:20.

It is preferable when the temperature, preferably the temperature of the mixture is from 160° C. to 350° C., from 170° C. to 300° C. and more preferably from 180° C. to less than 200° C., particularly when the hydroxycarboxylic acid employed is 3-hydroxypropionic acid.

The method according to the invention is preferably carried out while stirring or while using a means having the same effect in order to achieve commixing that is as close to complete as possible.

The metal salt is preferably an alkali metal salt or an alkaline earth metal salt. When the metal salt is a metal carbonate, the metal salt is preferably an alkali metal salt, more preferably a sodium or potassium salt and most preferably a potassium salt. When the metal salt is a metal salt of formula (I), said salt is preferably selected from $KH_2PO_4$, $K_2HPO_4$, $Na_2HPO_4$ and $BaHPO_4$ and mixtures of one or more, preferably of two, of these salts, more preferably mixtures of $KH_2PO_4$, $K_2HPO_4$ or $Na_2HPO_4$ with $BaHPO_4$. When mixtures of metal salts of formula (I) are used, it is preferable to use mixtures of metal salts where the salts are present in equimolar ratios. Salts of formula (I) may, for example, be produced as described in WO 2013/155245 A2 or obtained from the sources identified in this document.

The employed hydroxycarboxylic acid to be dehydrated and the hydroxycarboxylic acid on which the metal salt is based are preferably identical. When different hydroxycarboxylic acid feedstocks are employed successively, the mixture is advantageously likewise replaced.

The mixture preferably comprises at least one polymerization inhibitor (compound that inhibits polymerization of the acrylic acid and/or of the hydroxycarboxylic acid employed), preferably selected from phenothiazine, hydroquinone and its methyl ethers, and mixtures thereof, more preferably hydroquinone and/or its methyl ethers, most preferably hydroquinone and p-methoxyphenol. It is also possible to use a copper inhibitor, for example copper carbamate or else pulverulent copper, either in addition or as an alternative to the aforementioned polymerization inhibitors. The fraction of the sum total of polymerization inhibitors in the liquid mixture is preferably from 0.05% to 2.5% by mass, preferably from 0.1% to 0.5% by mass.

The method according to the invention may be carried out at atmospheric pressure or subatmospheric pressure. It is preferable when the method is carried out at subatmospheric pressure. It is preferable when the pressure above the liquid mixture is below 500 mbar, preferably below 200 mbar and more preferably from 50 to 100 mbar.

The contacting of the hydroxycarboxylic acid to be dehydrated and the mixture may be performed such that the hydroxycarboxylic acid to be dehydrated is passed either onto the mixture or into the mixture. The hydroxycarboxylic acid to be dehydrated is preferably introduced into the mixture. It is preferable when the introduction of the hydroxycarboxylic acid to be dehydrated into the liquid mixture is performed via an introduction point disposed no less than 5% and no more than 75%, preferably 10% to 30%, below the surface of the mixture based on the total height of the liquid at this point.

The employed $C_3$ hydroxycarboxylic acid to be dehydrated is preferably 3-hydroxypropionic acid or lactic acid, preferably lactic acid.

The method according to the invention may be carried out in all apparatuses known to those skilled in the art in which a fluid may be heated to a desired reaction temperature, it being preferable when the apparatus can have a pressure applied to it that is sufficient to keep the reaction components liquid under the desired temperature conditions.

The hydroxycarboxylic acid to be dehydrated may be contacted with the mixture as a pure substance or in the form of a composition. The hydroxycarboxylic acid to be dehydrated is preferably employed as a composition. This composition preferably comprises water in addition to the hydroxycarboxylic acid to be dehydrated. It is preferable when the water content of the composition based on the sum total of hydroxycarboxylic acid to be dehydrated and water is from 10 to 55 wt %, preferably from 20 to 50 wt %.

The composition may further comprise a metal salt, preferably the same salt that was used to produce the mixture. The fraction of the metal salt in the composition is preferably from 0.01 to 1 wt %, preferably from 0.2 to 0.5 wt % based on the composition.

The composition may additionally comprise polymerization inhibitors, preferably the polymerization inhibitors identified as preferable hereinabove. The fraction of the polymerization inhibitors in the composition is preferably from 0.05% to 2.5% by mass, preferably from 0.1% to 0.5% by mass, based on the composition.

The present invention is more particularly described with reference to the figures FIG. 1 to FIG. 3 without any intention to restrict the invention to this embodiment.

FIG. 1 is a schematic diagram of the experimental set-up used in Example 1. Two glass tubes lead into a heatable round-bottom flask R equipped with a stopper and a blade-stirrer. The left-hand glass tube G1 is long enough to protrude into any liquid mixture in the round-bottom flask and is used to supply substances into the round-bottom flask. The right-hand glass tube G2 is shorter and only reaches the gas space. The right-hand glass tube G2 is connected to a vacuum pump V. Between the vacuum pump and the round-bottom flask there is a cold trap C in which samples of condensed substances exiting the round-bottom flask via the right-hand glass tube may be taken in fractionated fashion.

Figure 2:
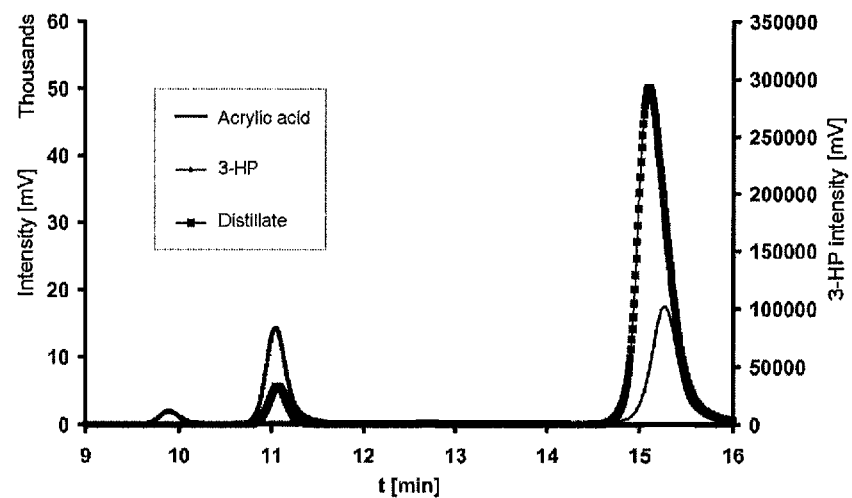
FIG. 2 is a chromatograph of Example 1.
Figure 3:
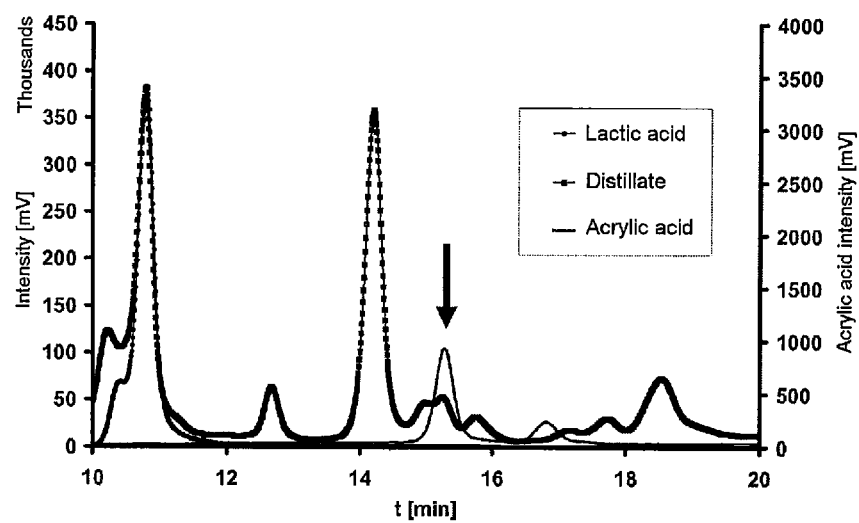
FIG. 3 is a chromatograph of Example 2.

The figures FIG. 2 and FIG. 3 are chromatograms of the analyzed samples from Examples 1 and 2.

The present invention is illustratively described in the examples which follow without any intention of limiting the invention, whose scope is determined by the entire description and the claims, to the embodiments referred to in the examples.

EXAMPLES

Example 1

Dehydration of 3-Hydroxypropionic Acid (3-HP) to Afford Acrylic Acid

Into a 500 ml round-bottom flask belonging to an experimental apparatus of the type shown in FIG. 1 were initially charged 1 mol of 3-HP as a 60 wt % solution in water, 0.4 mol of $K_2CO_3$, 2 g of hydroquinone and 2 g of p-methoxyphenol (MEHQ). With stirring, this mixture was heated to 180° C. over one hour using a heating mantle and the water thereby distilled over was discarded. Via glass tube G1 which protruded about 1 cm into the liquid mixture, which mixture had a height of 5 cm at this point, about 120 g/h of a composition comprising 0.1% by mass of hydroquinone, 0.1% by mass of MEHQ, and 3-HP up to 99.8% by mass as a 22 wt % solution in water were introduced into the flask using an HPLC pump. A vacuum pump was used to apply via glass tube G2 an under pressure of about 95 mbar for the duration of the experiment. The gaseous substances withdrawn via G2 were liquefied and collected in fractionated fashion via a glass condenser (descending intensive condenser). The remaining vaporous low boilers were condensed in a cold trap. The isolated fractions were analyzed by HPLC. This was done using a Shimadzu Prominence instrument and a Nucleogel Sugar 810 H column (MACHEREY-NAGEL). The eluent employed was a 5 mM $H_2SO_4$ solution (0.7 mL/min). As is shown by the analysis, all distillates and the vapors condensed in the cold trap contain primarily free acrylic acid as well as small amounts of unconverted 3-HP and water (FIG. 2).

Example 2

Dehydration of Lactic Acid to Afford Acrylic Acid

Example 1 was repeated except that a 60 wt % aqueous solution of lactic acid was used in place of the aqueous 3-HP solution. Comparison of the distillate chromatogram with that of acrylic acid demonstrated successful conversion into acrylic acid for this experiment too (FIG. 3).

As is apparent from the HPLC analyses, the method according to the invention produced acrylic acid from both 3-HP and lactic acid.

Example 3

Dehydration of Lactic Acid to Afford Acrylic Acid

Into a 500 ml round-bottom flask of an experimental apparatus of the type shown in FIG. 1, which was equipped with a heating means, were initially charged 1 mol of lactic acid as a 90 wt % solution in water, 2 mol %, based on the lactic acid, of salt, 2 g of hydroquinone and 2 g of p-methoxyphenol (MEHQ). With stirring, this mixture was heated to 180° C. over one hour using a heating mantle and the water thereby distilled over was discarded. Via glass tube G1 which protruded about 1 cm into the liquid mixture, which mixture had a height of 5 cm at this point, about 120 g/h of a composition comprising 0.1% by mass, based on the composition, of hydroquinone, 0.1% by mass of MEHQ and lactic acid up to 99.8% by mass as a 45 wt % solution in water were introduced into the flask using an HPLC pump. The pot temperature was set to about 300° C. during the reaction. A vacuum pump was used to apply an under pressure via glass tube G2 of more than 100 mbar and less than 1 bar for the duration of the experiment. The gaseous substances withdrawn via G2 were liquefied and collected in fractionated fashion via a glass condenser (descending intensive condenser). The remaining vaporous low boilers were condensed in a cold trap. The isolated fractions were analyzed by HPLC. This was done using a Shimadzu Prominence instrument and a Nucleogel Sugar 810 H column (MACHEREY-NAGEL). The eluent employed was a 5 mM $H_2SO_4$ solution (0.7 mL/min). The results are listed in table 1.

The salts employed were produced as per WO 2013/155245 A2 or obtained from the sources identified therein or from comparable sources in the highest obtainable purity.

TABLE 1

Results of the Example 3 experiments

| Ex. | Salt | Pot temperature | Reaction time | Acrylic acid yield [mol %] |
|---|---|---|---|---|
| 3a | $K_2HPO_4$ | ~300° C. | 5.3 h | 1.3 |
| 3b | $KH_2PO_4$ | ~300° C. | 5.0 h | 0.4 |
| 3c | $BaHPO_4$ | ~300° C. | 4.7 h | 1.2 |
| 3d | $K_2HPO_4$ $BaHPO_4$ | ~300° C. | 4.4 h | 0.1 |
| 3e | $KH_2PO_4$ $BaHPO_4$ | ~300° C. | 5.5 h | 0.3 |
| 3f | $Na_2HPO_4$ $BaHPO_4$ | ~300° C. | 4.8 h | 0.1 |

Experiments 3d to 3f employed mixtures of the salts in a molar ratio of 1:1.

The experiments according to Examples 3a to 3f show that liquid-phase dehydration of lactic acid is possible.

What is claimed is:
1. A method for producing acrylic acid by the dehydration of a $C_3$ hydroxycarboxylic acid, comprising the step of contacting the $C_3$ hydroxycarboxylic acid with a liquid mixture at a temperature of more than 150° C., wherein the liquid mixture comprises at least one alkali metal salt or alkaline earth metal salt of a $C_3$ hydroxycarboxylic acid, and water.
2. The method as claimed in claim 1, wherein the temperature of the mixture is from 160° C. to 300° C.
3. The method as claimed in claim 1, wherein the hydroxycarboxylic acid metal salt is produced using a metal carbonate or one or more metal salts of formula (I)

$$M^{z+}{}_x H_{3-x*z} PO_4{}^{z*x-} \quad (I)$$

where x=1 or 2, z=1 or 2 and M=metal, with the proviso that when z=2, x=1 wherein the metal is an alkali metal or alkaline earth metal.
4. The method as claimed in claim 1, wherein the hydroxycarboxylic acid to be dehydrated and the hydroxycarboxylic acid on which the hydroxycarboxylic acid metal salt is based are identical.
5. The method as claimed in claim 1, wherein the mixture comprises at least one polymerization inhibitor.
6. The method as claimed in claim 5, wherein the fraction of the sum total of polymerization inhibitors in the liquid mixture is from 0.05% to 2.5% by mass.
7. The method as claimed in claim 1, wherein the pressure above the liquid mixture is below 500 mbar.

8. The method as claimed in claim 1, wherein the contacting of the hydroxycarboxylic acid to be dehydrated and the mixture is performed such that the hydroxycarboxylic acid is introduced into the mixture.

9. The method as claimed in claim 8, wherein the introduction of the hydroxycarboxylic acid to be dehydrated into the liquid mixture is performed via an introduction point disposed no less than 5% and no more than 75% below the surface of the mixture based on the total height of the liquid at this point.

10. The method as claimed in claim 1, wherein the employed $C_3$ hydroxycarboxylic acid to be dehydrated is selected from 3-hydroxypropionic acid and lactic acid.

11. The method as claimed in claim 5, wherein the polymerization inhibitor is selected from hydroquinone and p-methoxyphenol.

12. The method as claimed in claim 5, wherein the fraction of the sum total of polymerization inhibitors in the liquid mixture is from 0.1% to 0.5% by mass.

13. The method as claimed in claim 1, wherein the pressure above the liquid mixture is from 50 to 100 mbar.

14. A method for producing a superabsorbent polymer comprising a step of producing a monomer component containing an acrylic acid made by dehydration of a $C_3$ hydroxycarboxylic acid, wherein the dehydration is achieved by contacting, at a temperature of more than 150° C., a hydroxycarboxylic acid with a liquid mixture at this temperature and comprises at least one metal salt of a $C_3$ hydroxycarboxylic acid, and water.

15. The method as claimed in claim 14, wherein the employed $C_3$ hydroxycarboxylic acid to be dehydrated is selected from 3-hydroxypropionic acid and lactic acid.

* * * * *